(12) United States Patent
Engebretson

(10) Patent No.: US 6,978,688 B2
(45) Date of Patent: Dec. 27, 2005

(54) SEMIPERMEABLE MEMBRANE-BASED SAMPLING SYSTEMS

(75) Inventor: Daniel S. Engebretson, Fargo, ND (US)

(73) Assignee: Dakota Technologies, Inc., Fargo, ND (US)

(*) Notice: Subject to any disclaimer, the term of this patent is extended or adjusted under 35 U.S.C. 154(b) by 0 days.

(21) Appl. No.: 10/698,715

(22) Filed: Oct. 31, 2003

(65) Prior Publication Data

US 2004/0089079 A1    May 13, 2004

Related U.S. Application Data

(60) Provisional application No. 60/422,515, filed on Oct. 31, 2002.

(51) Int. Cl.[7] ............... G01N 1/10; G01N 1/12; B01D 61/00
(52) U.S. Cl. ............... 73/863.23; 73/64.56; 73/863.71
(58) Field of Search ............... 73/64.56, 863, 73/863.21, 863.51, 863.71

(56) References Cited

U.S. PATENT DOCUMENTS

| | | | | | |
|---|---|---|---|---|---|
| 3,830,106 | A | * | 8/1974 | Gardiner et al. | 73/863.23 |
| 4,692,287 | A | * | 9/1987 | Timmons | 264/41 |
| 4,759,227 | A | * | 7/1988 | Timmons | 73/863.23 |
| 5,000,051 | A | * | 3/1991 | Bredemeier | 73/863.23 |
| 5,147,561 | A | * | 9/1992 | Burge et al. | 210/747 |
| 5,334,189 | A | * | 8/1994 | Wade | 604/890.1 |
| 5,411,087 | A | * | 5/1995 | Taylor | 166/264 |
| 5,465,628 | A | * | 11/1995 | Timmons | 73/864.34 |
| 5,582,794 | A | * | 12/1996 | Hagiwara et al. | 422/48 |
| 5,639,956 | A | * | 6/1997 | Christy | 73/19.01 |
| 5,804,743 | A | | 9/1998 | Vroblesky et al. | |
| 5,889,217 | A | * | 3/1999 | Rossabi et al. | 73/864.74 |
| 5,996,423 | A | | 12/1999 | Baghel et al. | |
| 6,148,914 | A | | 11/2000 | Guleze | |
| 6,196,074 | B1 | * | 3/2001 | Varhol | 73/863.23 |

OTHER PUBLICATIONS

Vroblesky et al., "Field Tests of Diffusion Samplers for Inorganic Constituents in Wells and at a Ground-Water Discharge Zone", 2002.*
Einfield et al., "Environmental Technology Verification Report—Ground WAter Sampling Technologies", Aug. 2000.*

* cited by examiner

Primary Examiner—Hezron Williams
Assistant Examiner—David A. Rogers
(74) Attorney, Agent, or Firm—Dorsey & Whitney LLP

(57) ABSTRACT

The device and methods relate to a sampling device for obtaining samples of analytes in a difficult-to-reach sampling location, such as below ground or underwater, and transporting the sample to an accessible delivery or collection site. The sampling device comprises a semipermeable membrane-based sampling chamber, which can be positioned under the ground or water surface where analytes of interest can permeate into the chamber through the semipermeable membrane. Transfer channels, which communicate with the sampling chamber, is used to transport the sample to the surface for analysis without removing the chamber from the sampling location.

20 Claims, 8 Drawing Sheets

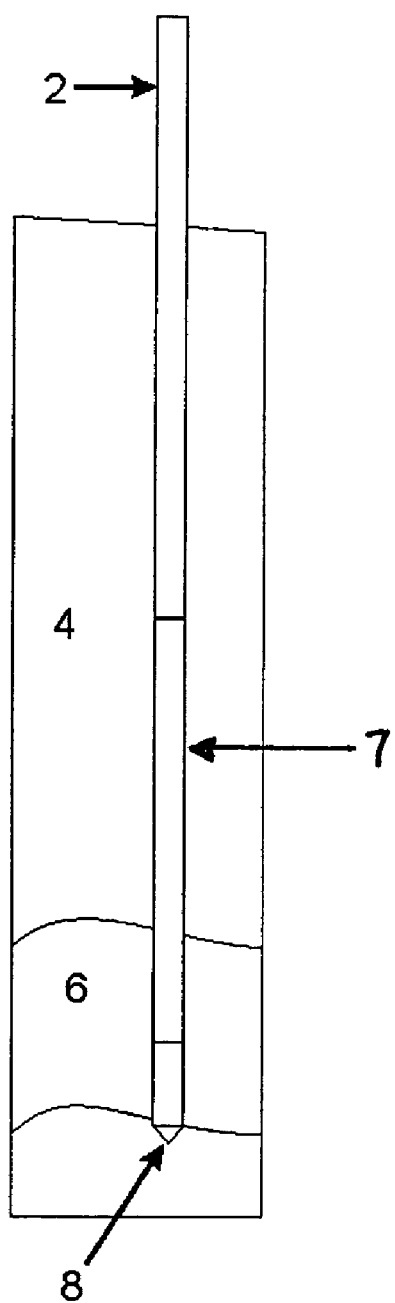
FIG._1

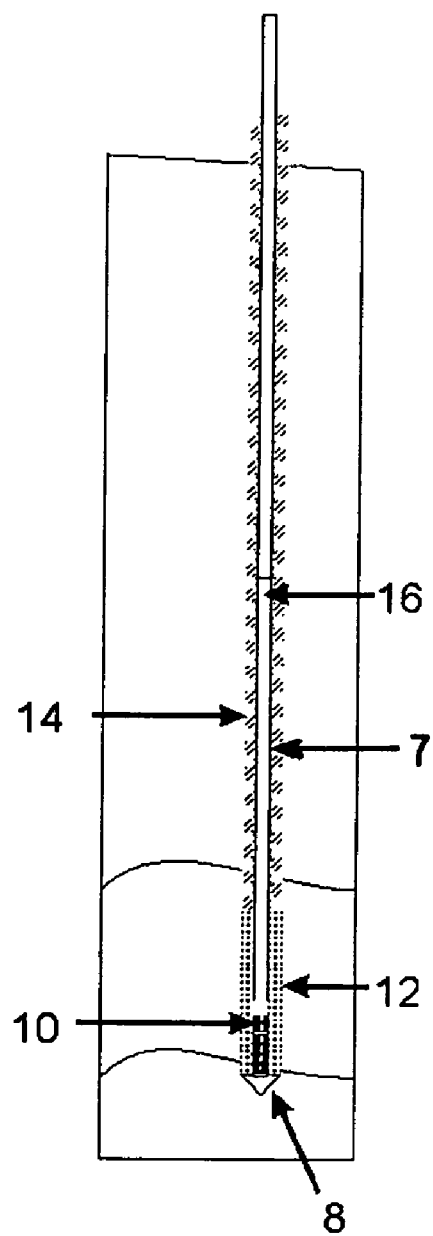
FIG._2

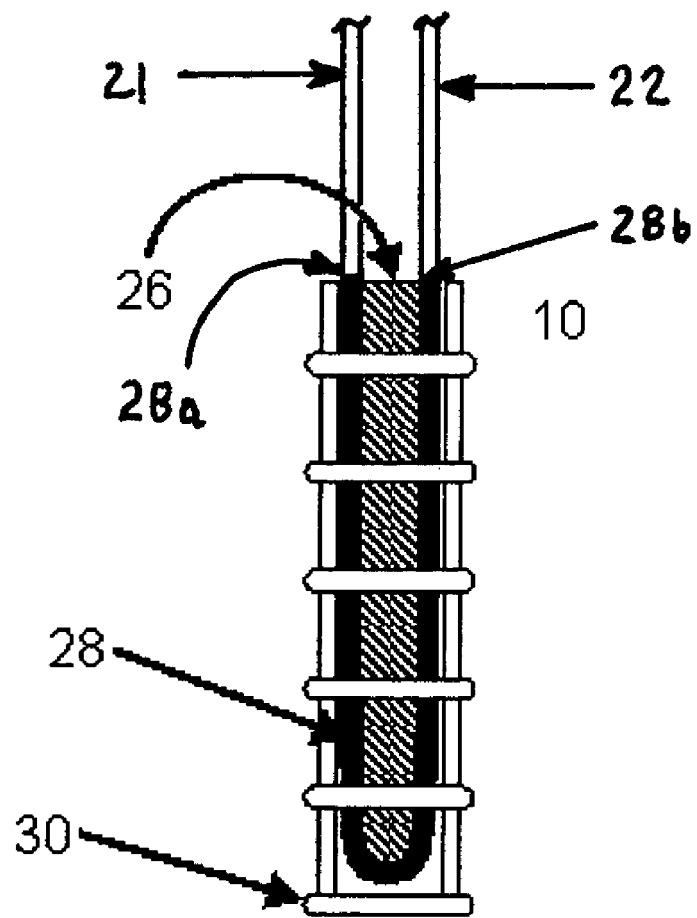
FIG._3

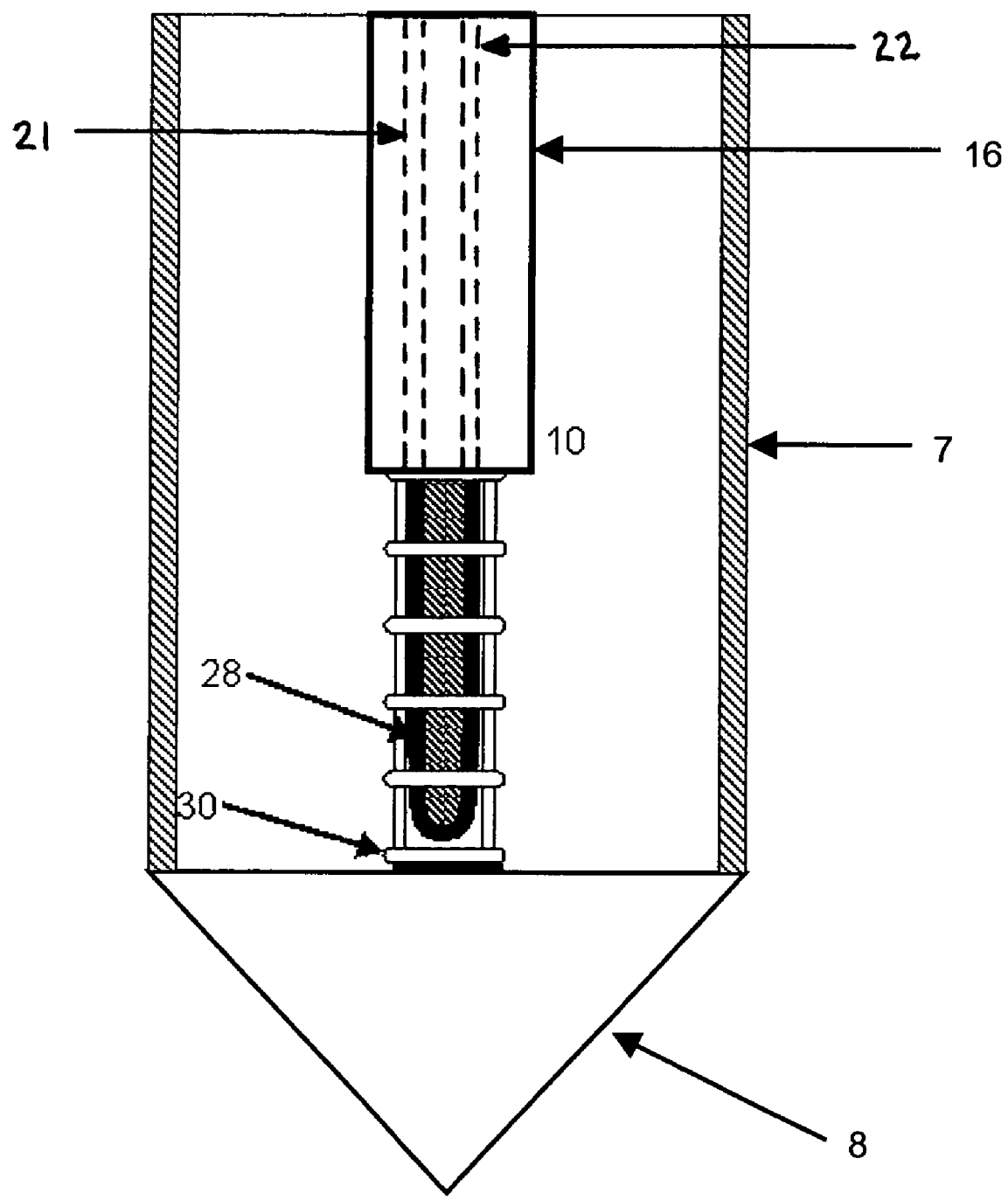
*FIG._4*

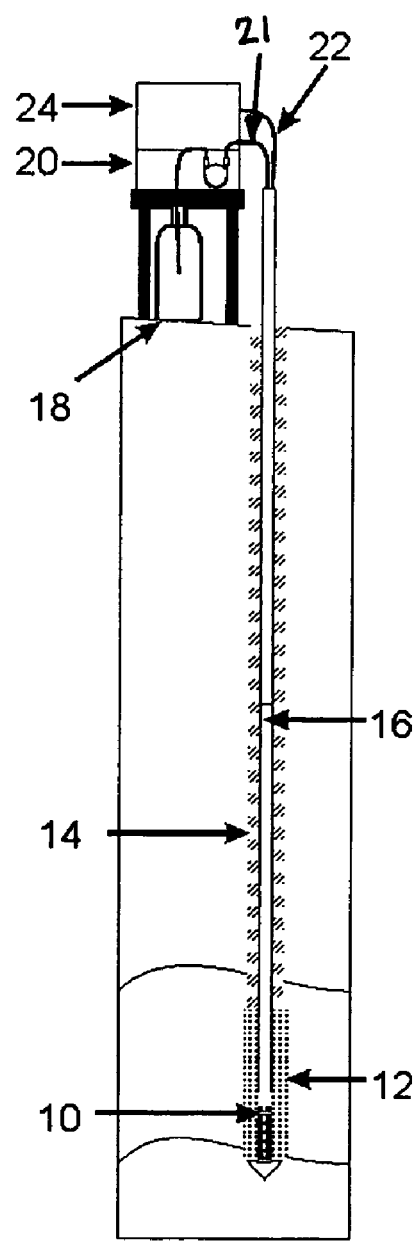
FIG._5

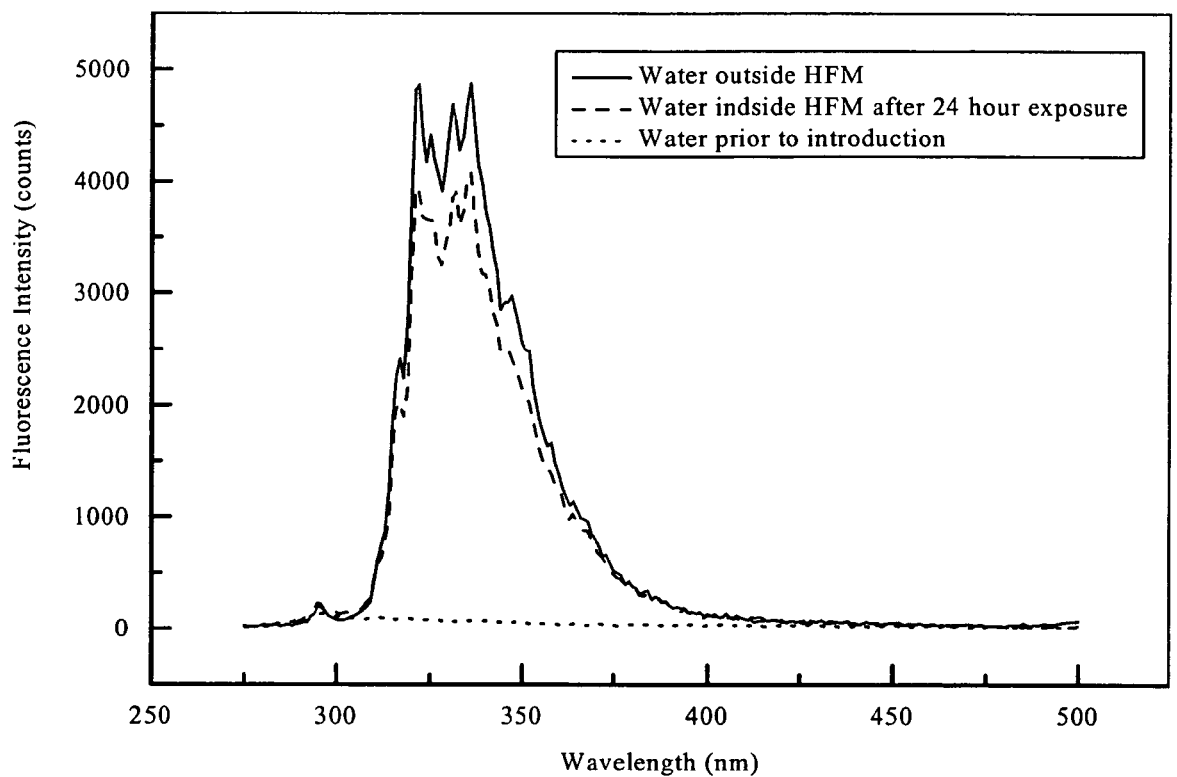
FIG._6

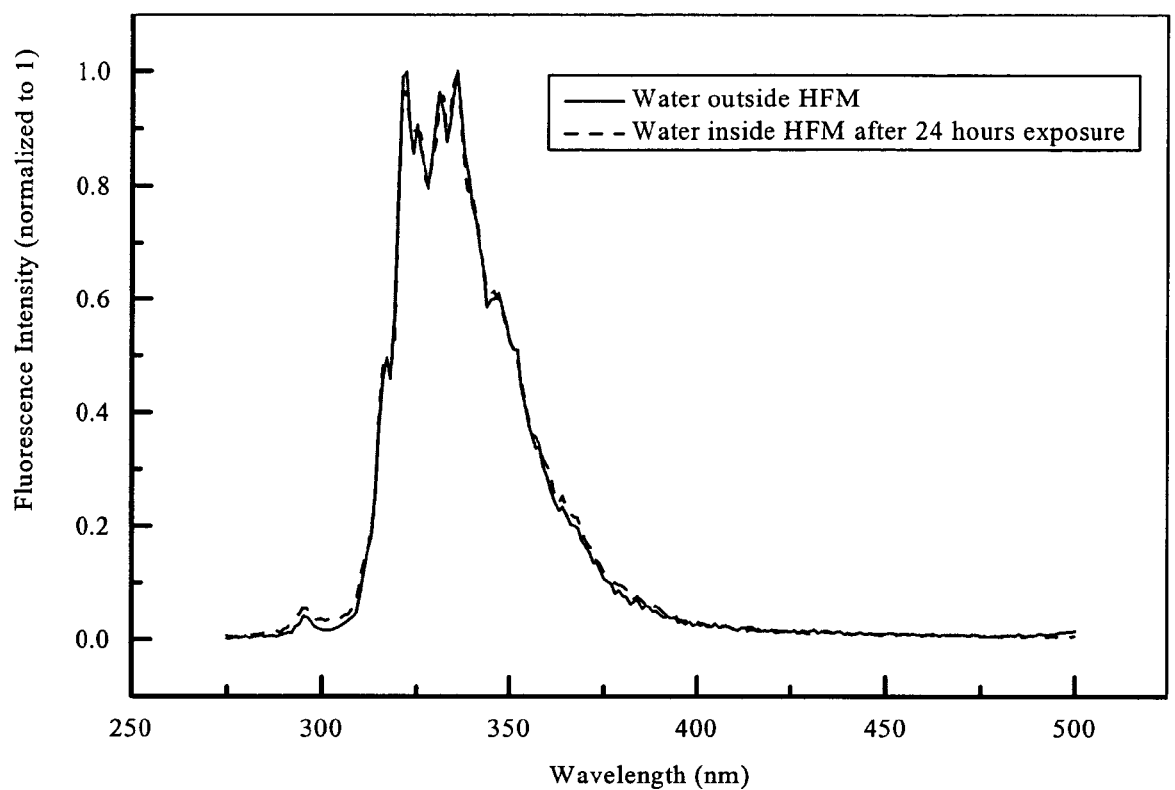
FIG._7

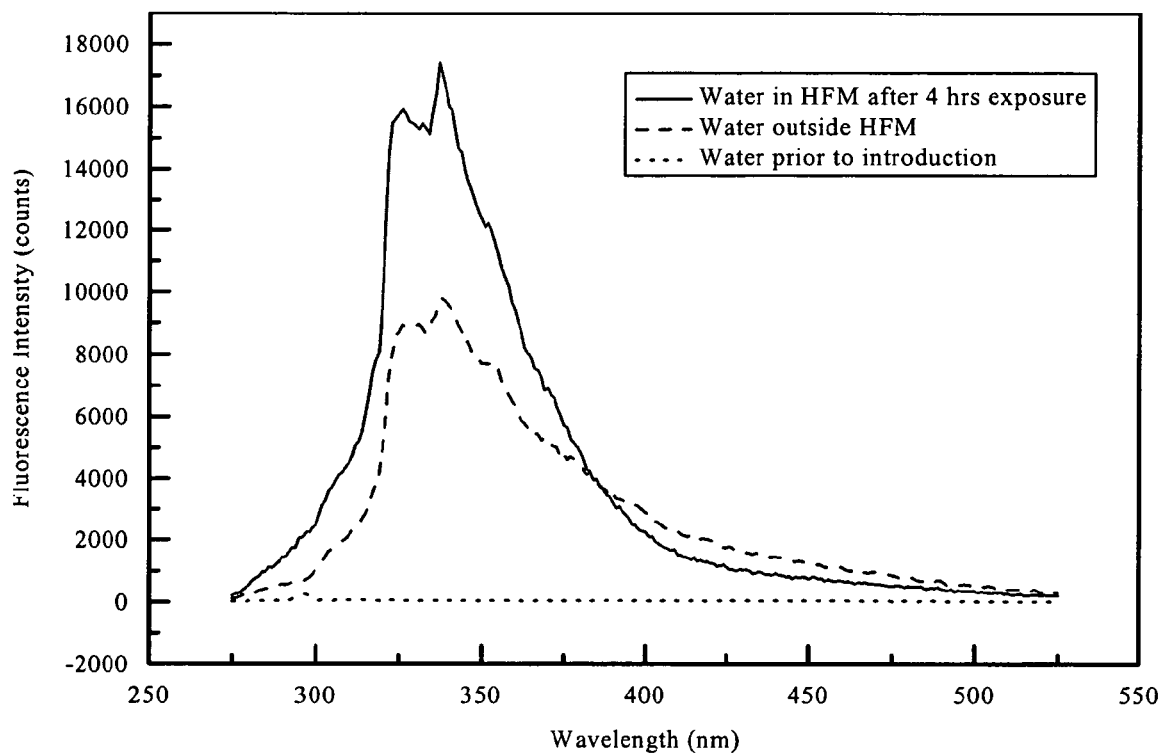
FIG._8

SEMIPERMEABLE MEMBRANE-BASED SAMPLING SYSTEMS

CROSS-REFERENCES TO RELATED APPLICATIONS

This application claims the benefit of U.S. Provisional Application No. 60/422,515 filed Oct. 31, 2002, the entire contents of which is incorporated herein by reference.

TECHNICAL FIELD

Devices and methods relate to a system for obtaining a sample of the environment within difficult-to-reach or relatively inaccessible locations, such as below the ground surface or underwater, and transporting the sample to a sample collection or delivery site for analysis.

BACKGROUND

The costs associated with monitoring subsurface conditions, such as the contents of groundwater (including monitoring well installation, sampling, analysis, and decommissioning), are often expensive and thus reduce resources that would otherwise be applied to other endeavors such as prevention and remediation. In addition, the data collected from monitoring wells is often difficult to interpret due to obstacles in obtaining a representative sample and the infrequency of sampling.

Conventional methodology is problematic for several reasons. For instance, standard operating procedure calls for the removal (purging) of 3–10 casing volumes of water from the monitoring well before collecting the sample. The amount actually collected for analysis is typically 1/1000 th or less of the total volume of water removed from the well. The purging process, designed to ensure that the sample is representative of the formation, is slow and cumbersome. Furthermore, the water removed sometimes must be treated as a hazardous waste, thereby incurring even more expense. Data quality due to loss of volatile analytes is also a serious concern because the sample is subjected to many procedures prior to analysis. These procedures include, for example, transfer to a container, transport to the off-site laboratory, storage, sample dilution, and clean-up or preconcentration. The data quality problem is especially acute for low contaminant concentrations, such as less than 50 $\mu$g/L of contaminant.

Improvement has been made in groundwater sampling. For instance, U.S. Pat. Nos. 5,804,743 and 5,996,423 describe the use of sampling bags made of semi-permeable membrane materials to collect volatile organic components in groundwater. The bags are lowered into a monitoring well, and the volatile organic components in the water allowed to permeate through the membrane into a reference fluid contained in the bags. The sampling bags are then withdrawn from the well and the fluid contents of the bags are analyzed for the presence of the dissolved volatile components.

Placing a sampling apparatus within a well eliminates the need to pump water to the surface for study and thus simplifies sampling. However, several problems are associated with this approach. For example, volatiles may escape from the water column or soil matrix into the headspace of the well, thereby reducing the amount of volatile substance available to achieve an equilibrium value between the inside and outside of the sample bag. In addition, when the sampling bag is removed from a well for analysis, some losses of volatile components may occur in the transfer of sample from the sampling bag to a sample container for subsequent transport to a laboratory.

Improved methods and systems for monitoring subsurface conditions are therefore needed.

SUMMARY

The sampling system comprises a sampling device for obtaining a sample from a difficult-to-access sampling location, such as below ground or underwater, for detecting an analyte of interest. In one aspect, the sampling device comprises a chamber having a least one wall of the chamber defined by a semipermeable membrane. The membrane is permeable to the analyte of interest. A set of transfer channels communicates with the chamber and is used to transport the sample from the chamber to an accessible sample collection site. In one embodiment, the sample device comprises a first channel communicating with the chamber and a second channel communicating with the first channel through the chamber. The first and second channels are used to transport a carrier fluid containing the sample to be analyzed from the sampling location to the sample collection site without removal of the chamber. In one embodiment, the semipermeable membrane is in the form of a tube, where the inner space of the tube comprises the chamber. Exemplary semipermeable membranes of this type include silicone and TEFLON tubing.

The chamber and/or parts of the transfer channels communicating with the chamber may be protected by a cage structure, which protects the chamber and the channels during positioning of the sampling device and during the sampling process. In addition to the cage, the sampling device may optionally have a protective layer or housing, which surrounds the transfer channels. This protective layer maintains the integrity of the transfer channels and/or protects the channels from physical factors of the sampling environment, such as pressure and temperature. The layer or housing may be flexible, semi-rigid, or rigid and may be made of polymeric material, metal, or other suitable materials.

The sampling device may further comprises a shell or casing, which surrounds the sampling chamber and transfer channels, and protects the sampling device from damage while being placed in the sampling site, such as underground or underwater. The shell is removable or retractable to permit exposure of the chamber to the sampling environment.

The sampling device further comprises a source of pressurized fluid connected to one of the transfer channels for driving the carrier fluid from the chamber through the other transfer channel to a sample collection site, where the sample is accessed for analysis. In one embodiment the source of the pressurized fluid is a pump connected, directly or indirectly, to the transfer channel. The transfer channel from which the sample is delivered may be connected to a sample collector, such as an automated sample collector for collecting the sample, or connected to an analytical instrument for detecting the analyte of interest. In another embodiment, the transfer channel may be connected to a trap, which binds or traps the analyte of interest for subsequent analysis.

The methods for obtaining a sample for detecting an analyte of interest comprises positioning the sampling device in the desired sampling location, various methods of which are known in the art. For example, where the sample environment is underground, a preformed path can be made, such as by drilling. In another embodiment, the sampling device is inserted directly underground without preparing a preformed path by use of an insertion probe comprising the sampling device. Where the sampling environment is underwater, the device may be weighted and placed at the desired depth. Upon reaching the desired site, the shell encasing the chamber and the transfer channels is retracted to allow contact of the semipermeable membrane with the environment. For below ground applications, the space left upon withdrawal of the shell is optionally filled with an inert material, which fills the space but allows flow of material to be sampled onto the sampling device. In addition, the space between the sampling chamber and the ground surface can be sealed to prevent contamination or alteration to the monitoring surroundings.

After positioning the sampling device in the sampling location, the method further comprises allowing analytes to permeate through the semipermeable membrane into the chamber containing the carrier fluid. The carrier fluid is then transported from the chamber to the sample collection site through one of the channels and examined for presence of the analyte of interest.

A single sampling device may be used to sample a single location. For studies of more extensive regions, an array of the sampling systems or sampling units may be positioned in the desired area. Each sampling device may be placed in a different vertical and/or horizontal location, which permits examination of the spatial distribution of the analyte of interest in the defined region. This type of assay systems can be used to monitor the spatial pattern of underground contamination or other conditions.

A variety of analytes may be sampled by the device and systems described herein. These include, but are not limited to, volatile and semivolatile organic compounds, metals, inorganic ions, biological materials (e.g., proteins, viruses, bacteria, etc.), and gases. The ability to sample the environment without removal of the sampling device reduces the difficulties of monitoring difficult-to-access or hard-to-reach locations, such as below ground or underwater.

BRIEF DESCRIPTION OF THE DRAWINGS

FIG. 1 illustrates a sampling system comprising a sampling device installed at an underground location.

FIG. 2 illustrates a sampling system with the protective shell retracted to expose the sampling device to the sampling environment.

FIG. 3 illustrates a semipermeable membrane-based sampling chamber with supporting accessories.

FIG. 4 illustrates a tip assembly used to insert the sampling device into an undergrounnd sampling location.

FIG. 5 illustrates a sampling system connected to an analytical instrument and a pump or a source of pressurized fluid.

FIG. 6 shows data collected using a semipermeable membrane-based hollow-fiber sampler.

FIG. 7 shows normalized data of FIG. 6.

FIG. 8 represents laboratory data collected from a semipermeable membrane-based hollow-fiber sampler implanted in a coal tar saturated water solution.

DETAILED DESCRIPTION

The sampling systems described herein are used to detect analytes of interest, such as semivolatile organic compounds (SVOs) or volatile organic contaminants (VOCs), present in difficult-to-access or relatively inaccessible locations, such as in substrata (e.g., underground) or in fluid volumes (e.g., underwater). The sampling systems can also be used to sample a variety of fluids in the relatively inaccessible locations for the presence or absence of organic materials; for example, sampling a gas stream for the presence of contaminants, or sampling a liquid reactant stream in an industrial process for the presence of unreacted constituent materials. The systems are also useful for sampling a pool of waste or other stored materials for internal conditions. Other applications of the systems and devices include, but are not limited to, determination of pollutant sources and relative levels of corresponding pollutants, detection of episodic chemical releases, and in situ extraction of environmental contaminants for bioassay and/or immunoassay.

The sampling systems described herein permit obtaining of samples without the need to retrieve the sampling chamber used to collect the environmental sample. This reduces the difficulties of continuous monitoring of an underground or underwater environment and the complications associated with retrieving the sampling device, such as loss of the analyte of interest or contamination of the sample. The sampling system uses a chamber to collect a sample of the surrounding environment in a sampling location and incorporates channels to transport the sample from the chamber to a readily accessible sample collection site or to an analytical instrument for direct sample analysis. The use of a semipermeable membrane in the chambers allows selective sampling of the environment for an analyte of interest.

Accordingly, in one embodiment, the sampling system or sampling device for detecting an analyte of interest comprises a chamber having a semipermeable membrane defining at least one wall of the chamber. The sampling device has a first channel, which communicates with the chamber, and a second channel, which communicates with the first channel through the chamber. Communication between the first and second channels via the chamber enables a carrier fluid to be transported or carried from the chamber to a sample delivery site.

As described herein, the sampling chamber may be of different types and made of various materials. In one embodiment, the semipermeable membrane forms the chamber, such as a semipermeable membrane in the shape of a hollow fiber or tube. In this embodiment, the inner space of the tube forms the chamber. The sample to be tested is collected within the inner space and transported to the sample collection site via transfer channels, which in one aspect, are connected to the ends of the hollow fiber or tube.

In another embodiment, the walls of the chamber are made of a different material than the semipermeable membrane. The membrane is bonded, affixed, or sealed to the material forming the walls of the chamber to complete the chamber. The semipermeable membrane may be in the form of a sheet, or corrugated or folded in other shapes to increase the area of contact with the sampling environment. By way of example and not limitation, the chamber may be formed by a disc or cylinder of material in which one end comprises the semipermeable membrane. Thus, one side of the semipermeable membrane faces outside the chamber while the other side faces the inside of the chamber formed by the material. A first port or first opening is present on the chamber and is connected to and communicates with one of the transfer channels (e.g., first channel). A second port or second opening in the chamber is connected to and communicates with the other transfer channel (e.g., second channel). In the sampling device, communication between the transfer channels does not occur by flow of fluid through the semipermeable membrane, but occurs via the chamber formed by the semipermeable membrane. Ridges, ribs, or partitions may be included within the chamber to direct flow of carrrier fluid smoothly and efficiently throughout the chamber.

In another exemplary form of the chamber, the semipermeable membrane may be in the form of a cylinder and the ends of the cylinder sealed or capped with a platform or disc of material to complete the chamber. A supporting structure, either internal or external of the chamber, may be used to provide rigidity and stability to the cylinder of membrane. Thus, in this embodiment, the semipermeable membrane forms the sides of the cylinder. One of the platforms or discs at one end of the cylinder has a first port or first opening, which connects to the one of the transfer channels (e.g., first transfer channel). A second port or second opening in the chamber, which connects to the other transfer channel (e.g., second transfer channel), allows communication of the first and second channels via the chamber. The first and second ports may be on the same end of the cylinder. However, for optimal flow of carrier fluid through the chamber, and to decrease the presence of regions within the chamber where fluid flow is static, the first port is on one end of the cylinder while the second port is on the other end of the cylinder. Structures within the chamber, such as partitions and ridges, may be used to guide fluid flow throughout the whole of the chamber.

Generally, materials for making the chamber are chosen to withstand the environmental conditions to which the sampling device is exposed. Factors include, but are not limited to, pressure resistance, temperature resistance, chemical reactivity, inertness, etc. Suitable materials include, by way of example and not limitation, polymers (e.g., plastics, teflon, etc.), metal (e.g., stainless steel, titanium, aluminum, etc.), carbon composites (e.g., graphite), silicone, etc., and mixtures thereof. It is to be understood that the descriptions of the chamber and the semipermeable membrane are not intended to be limited to the described embodiments. Suitable materials for forming the chamber and various chamber designs will be apparent to those skilled in the art.

In the sampling device, an analyte of interest in the surrounding environment is capable of permeating into the sampling chamber through the semipermeable membrane. By "semipermeable membrane" as used herein refers to a membrane which is permeable to the analyte of interest but which excludes some other compound or analyte. Driven by a pressure, concentration, temperature, or other chemical potential, the analytes may cross the membrane by various mechanisms. Permeation, including pervaporation, occurs as a combination of dissolution (solubility) and diffusion processes. Separation by size occurs by sieving of the analyte through pores or cavities of defined size. Carrier mediated processes separate based on selective interaction of the analyte with a carrier compound in the semipermeable membrane. For use in the sampling device, the semipermeable membrane may be chosen to be selective such that the membrane allows the selective transfer across the membrane of one particular analyte or class of analytes out of a complex mixture.

Various types of semipermeable membranes may be used in the sampling device, and may be selected based on characteristics of porosity, morphology, surface properties, mechanical strength, temperature resistance, chemical resistance, selectivity, and permeability. In one embodiment, the semipermeable membrane is non-porous. By "non-porous membrane" herein refers to a membrane in which the analyte dissolves in the membrane and diffuses through the wall structure. Generally, the non-porous membrane has a surface or a body that does not contain pores or cavities for passage of analytes. Consequently, transport properties of molecules are determined by a diffusion mechanism in which the analyte dissolves in the membrane and diffuses through the membrane. The semipermeable membrane material can be chosen based on its partition coefficients with the analytes of interest.

In another embodiment, the semipremeable membrane comprises a porous membrane. By "porous membrane" as used herein refers to a membrane containing pores or cavities through which the analyte passes or diffuses. It is the size of the pore or cavities that determines the separation characteristics of the porous membrane. Various membrane pore sizes useful in the sampling device are macropores, which have pores greater than about 50 $\mu$m; mesopores, which have pore sizes less than about 50 $\mu$m but larger than about 2 nm; and micropores, which have pore sizes less than about 2 nm. Selectivity of the membrane is obtained when the size of the materials to be excluded is large relative to the pore size in the membrane. Semipermeable membranes comprising porous membranes are useful for sampling and detecting analytes of interest which pass through the pores or cavity, including dissolved solutes, solvents, and particulate materials. Particulates include inorganic, organic, and biological particulates.

In a further embodiment, the semipermeable membrane comprises a carrier membrane. Generally, in a carrier membrane, separation occurs by a carrier molecule which interacts with the analyte and transports the analyte across the membrane. Selectivity is obtained when the carrier molecule has a specific affinity for the target analyte or the class of target analytes. Exemplary carrier membranes include, by way of example and not limitation, ionic carrier membranes, containing ionizable functional groups bound to the polymeric structure of the membrane. Counter-ions that interact with the ionized functional groups can move freely through the membrane network, thus making the membrane selectively permeable to the counter-ion.

The semipermeable membranes may be made from various materials, as is well known in the art. These include, by way example and not limitation, cellulose esters and acetates, aliphatic and aromatic polyamides, polysulfone and polyether sulfone, polyethylene, polypropylene, ethylene vinyl acetate, polyacrylonitrile, polytetrafluoroethylene (PTFE), polyvinylidene fluoride, silicone, other polymers, or other synthetic or natural materials, including ceramics. For example, cellulose and polysulfone based membranes are made in non-porous or porous membrane forms; polyimide based membranes are made as non-porous membrane forms and are useful for gas analytes; polyacrylonitrile based membranes are made in porous membrane forms; and PTFE is made in both porous and non-porous membrane forms.

Ceramic based semipermeable membranes are useful in a variety of sampling environments and are especially applicable in sampling locations characterized by the presence of high temperature and/or high pressure. Ceramic based membranes also show resistance to acids, bases, and organic solvents. As with polymeric membranes, ceramic membranes are useful for separation of gas, liquids, and particulate material. Ceramic semipermeable membranes are typically prepared on the bases of $Al_2O_3$, $ZrO_2$, $TiO_2$ or other suitable materials, including various composites thereof, as is known in the art. Ceramic membranes functioning as carrier membranes, such as a ceramic conducting membrane (e.g., perovskite), may be used to sample certain charged analytes. Ceramic membranes selective for certain gases, such as oxygen and hydrogen, are described in U.S. Pat.

Nos. 6,569,226 and 6,623,714. Other types of exemplary ceramic membranes useful in the sampling device are described in U.S. Pat. Nos. 6,632,360; 6,582,495; 6,387,269; 6,440,309; 5,655,212; 5,215,943; 5,208,190; and 5,104,546, all of which are incorporated herein by reference.

Thickness of the semipermeable membrane is selected to be suitable for the analyte of interest and the sampling conditions. The semipermeable membranes may range from less than 1 micrometer to about 2 millimeter, preferably about 1 micrometer to about 1 millimeter, and more preferably about 40 to about 150 micrometer. As will be apparent to those skilled in the art, other thicknesses may be used as required by the specific application.

In one aspect, the semipermeable membrane takes the form of one or more hollow fibers or tubes which is capable of holding a carrier fluid. An exemplary semipermeable membrane comprises silicone tubing, such as Dow Corning Silastic. Silicone tubing has several desirable properties. It has historically been used to extract volatile and semivolatile compounds from environmental samples. It is inexpensive and readily available in convenient sizes and it is highly resistant to chemical and biological fouling.

Another exemplary embodiment of a semipermeable membrane is TEFLON AF. It has been reported that TEFLON AF membranes are impermeable to toluene but permeable to trichloroethylene. TEFLON AF is a product of E.I. du Pont de Nemours and Company. TEFLON AF is a family of amorphous fluoropolymers. The family retains the superior electrical, chemical resistant, and thermal properties associated with fluoropolymers. TEFLON AF polymers have high gas permeabilities. TEFLON AF and related polymers are described in U.S. Pat. Nos: 4,399,264; 4,485,250; 4,754,009; 4,935,477; 5,276,121; 5,326,839; 5,353,368; 5,324,889; 5,338,608; 5,310,838; 5,354,910; and 5,408,020, all of which are incorporated herein by reference.

Optionally, a membrane support structure may be present for holding the membrane or providing structural integrity to the chamber and the membrane. In one embodiment, when the semipermeable membrane is in the form of a tube, a protruding support material, such as in the form of a rod or dowel, is present to hold the tube in place. Grooves within the support material or clamps may be used to keep the tube and the membrane support together. In another embodiment, where the membrane forms the sides of a cylindrical chamber, membrane supports, such as porous polyethylene, may be used to form a wall in the cylinder, or positioned as slats at the edge of the chamber formed by the cylinder, onto which the semipermeable membrane is placed. Other variations of membrane supports are within the skill of those in the art and are to be emcompassed within the sampling device described herein.

The sampling device, particularly the chamber and connections of the channels to the chamber, may be protected by a cage, which may be made of any suitable material. Exemplary protective cages include, by way of example and not limitation, a metal cage (e.g, stainless steel, titanium, aluminum, etc.), a cage of polymeric material (e.g., PTFE, polyethylene, polypropylene, polycarbonate, etc.), a cage of carbor fiber composites, and/or reinforced cage with screening material (e.g., steel mesh screens), which permit flow of the material to be sampled around the sampling device.

In the sampling device, a first channel communicates with the chamber, and a second channel communicates with the first channel through the chamber. These transfer channels allow transport of a carrier fluid from the chamber to a sample delivery or collection site, where the presence of target analyte can be detected. For example, when the sampling location is underground, the first transfer channel and a second transfer channel is embedded in the subsurface strata and extend to the surface to the sample delivery site.

The first and the second transfer channels may be made of materials that sufficiently retain both the carrier fluid and the analytes of interest to permit sampling. As with the chamber, the channels may be made of suitable polymeric compound (e.g., polyethylene, polypropylene, PTFE, polycarbonate, etc.), metal (e.g., stainless steel, copper, nickel, titanium, aluminum, metal alloys, etc.), reinforced polymeric compound (e.g., polymer tubing surrounded with a metal braid, polymer tubing reinforced with weaved nylon, etc.) or any other suitable material (e.g., graphite composites), and may be semi-rigid or rigid to protect the channels from the physical forces in the surrounding environment, such as pressure. The first and second channels may be within a single structure, such as a steel or plastic rod containing the channels. In another embodiment, the first and second channels are separate, such as a first tube and a second tube. The transfer channels may be used to direct a continuous or periodic fluid stream through the sampling chamber, thereby purging the chamber and the semipermeable membrane. The channel need not be a single continuous channel, but may comprise shorter channels placed together to form a continuous channel. Sections comprising the channels may be combined together by various methods, including, by way of example and not limitation, clamping, bonding, or sealing to form the continuous channel.

It is to be understood that choosing the appropriate materials for the transfer channels are well within the skill of those in the art. Factors to consider include, among others, the permeability of the analyte of interest and carrier fluid in the material forming the channels, diffusion rate of the analyte through the channel material, chemical reactivity, and structural stability. Transfer channels made of materials that are impermeable to both the carrier fluid and the target analyte are generally desirable. In other embodiments, materials with limited permeability to the analyte of interest and/or carrier fluid may be used if the channels are made or constructed to retain the analyte of interest in sufficient amounts for purposes of sample analysis and analyte detection. By way of example and not limitation, the the transfer channels can be made of a material with limited permeability but the channel walls increased in thickness to limit diffusion of the analyte of interest inward or outward from the channels during the sampling process. In addtion, use of techniques, including, among others, calibration and purging of the sampling system prior to obtaining the sample, can be used to compensate for the effect of permeation through the walls of the transfer channels.

Generally, the lengths of these channels depend on the distance of the location of the sampling chamber from the sample delivery site. Thus, for instance, the lengths of the transfer channels can be at least 1, 5, 10, 20, 30, 40, 50, 60, 70, 80, 90 or 100 meters long. In some instances, the lengths may be longer (e.g., greater than 100 meters long) as permitted by the materials used for the transfer channel and as required to reach the sample delivery site from the chamber at the sampling location.

In one aspect, a single chamber communicates with the transfer channels. In another aspect, to enhance the sampling for the analyte of interest, a plurality of chambers communicates with the transfer channels. A plurality of chambers comprises at least two chambers. Thus, the sampling device may have at least 2, at least 5, at least 10, or at least 50 chambers. More may be added to obtain the desired sampling of the sampling environment. The use of multiple chambers provides a larger surface area for contact with the sampling enviroment, and thus enhances sampling and detection of the analyte of interest. Communication of multiple chambers with the transfer channels is done by ways known in the art. For instance, stream or flow splitters may be used to allow communication of a plurality of chambers with the transfer channels. As is known in the art, stream or flow splitters refers to connectors designed to split a stream of fluid from a channel or join streams together, such as with a "Y" configured splitter for two chambers. The plurality of chambers may be arranged in an array, including, by way of example and not limitation, linear, circular, triangular, square, hexagonal, or other array arrangements as desired depending on the types of splitters used.

As will be appreciated those skilled in the art, the sampling system may comprise additional channels in addition to the first and second transfer channels, where each set of transfer channels communicates with different chambers (or sets of chambers if flow splitters are used) in the sampling device. By way of example and not limitation, a third and a fourth transfer channel is used to communicate with a second chamber in a sampling device already containing a first channel, second channel, and a first chamber. The semipermeable membranes on the different chambers may be the same or different. Use of different semipermeable membranes in the different chambers allows sampling for different types of analytes present in the sampling location. By this configuration, a single device at a single location can be used to sample and detect different analytes of interest. Thus, a single sampling device can have a plurality of sampling chambers for sampling the analytes of interest. Other variations may be made in view of the embodiments described herein.

To protect the transfer channels from the sampling environment and/or maintain the channels as a single unit, the channels may be surrounded by a protective layer or a protective housing. The optional protective layer or housing surrounds the transfer channels and helps to protect the integrity of the channels during positioning of the sampling device in a sampling location and/or protects the transfer channels from collapsing under the pressure of the environment, particularly underground or underwater, after a shell, as described below, is removed. A variety of materials is useful for this purpose, and include, by way of example and not limitation, a layer of flexible polymeric sheet placed around the channels (e.g., polyethylene tape), a sheath or sleeve of protective material, or a semi-rigid or rigid housing which surrounds the channels. Exemplary forms of the protective layer include polymeric tape; flexible tubing in which the channels are housed; semi-rigid or rigid plastic or other types of polymeric (e.g., PVC, teflon, etc.) tubing; or a semi-rigid or rigid metal housing (e.g., rigid, corrugated, or braided metal tubing). The housing may be in the form of shorter sections, which may be placed together to protect the channels, as described below for the protective shell.

In a further embodiment, the sampling device comprises a shell, which is also used to protect the transfer channels. The shell may encase the transfer channels directly or may encase the transfer channels when they are surrounded by the protective layer. The shell, a semi-rigid or rigid casing, such as a rigid plastic or metal casing, protects the sampling device when placing or positioning the sampling device in the sampling location. The shell further covers or encases the chamber having the semipermeable membrane and protects it from damage during the positioning process. The shell is removable or retractable to allow contact of the sampling device with the environment to be monitored. In order to facilitate protection of the sampling device in far-removed locations (e.g., greater than about 5 meters), the shell may be in the form of shorter sections (as compared to the length of transfer channels) which can be attached together. Each section can be added as the probe is inserted further from the sample delivery site. The sections may be attached to each other by various methods, including, by way of example and not limitation, clamps which join sections of the shell; shells which screw together to form a continuous shell; welding or bonding of the shells together, the use of ferrules on the outside or inside of the shell sections for mating the sections together; or presence of grooved regions on the outer edges of the shell which allow one shell section to mate with another shell section.

The transfer channels allow transfer of carrier fluid from the chamber to the sample delivery site. Suitable carrier fluids for this invention include, but are not limited to, any fluid that is capable of dissolving the analytes of interest, such as a liquid or gas. Exemplary fluid carriers include, by way of example and not limitation, water or aqueous solutions, such as solutions of variable pH and ionic strength; polymeric solutions, such as polyethylene glycol; and organic solvents, such as methanol, ethanol, and isopropyl alcohol. Carrier fluids may also comprise mixtures of various carrier fluids. Suitable carriers are described in Booji, K. et al., *Chemosphere* 46:1157–1161 (2002), incorporated herein by reference.

In another embodiment, the fluid carrier is a gas or a mixture of gaseous fluid, which may be used to transport a gaseous analyte of interest. Exemplary gases useful as a carrier include, by way of example and not limitation, air, noble gases (e.g., helium, argon, etc.), nitrogen, carbon dioxide, chlorofluorocarbons, hydrochlorofluorocarbons, etc. Generally, gases to be used are inert with the analyte of interest, although in certain instances, the reaction products of the gas and analyte may be used to detect presence of the analyte of interest.

The carrier fluid contained in the sampling chamber is transported via the transfer channels to a sampling location, where the sample can be accessed without removing the sampling chamber. The analytes of interest present in the carrier fluid can then be analyzed. A pump or a source of pressurized air or liquid, or other fluid, can be attached to one or both of the transfer channels to facilitate the transport of the carrier fluid to the sample collection site.

In one embodiment, one of the transfer channels is connected to a sample collector, which collects and stores the sample in a vessel or container for subsequent analysis. If the analyte is volatile, sample containers which limit loss of analytes from the samples are used. The sample collection containers may include an additive, such as a stabilizing compound, if the analyte of interest is unstable or chemically reactive. Generally, the sample collector may be automated to collect samples at periodic intervals. Samples are automatically dispensed into a vessel or container, which may be sealed by the automated sample collector to preserve and limit loss of the analyte prior to analysis. Gases may be placed into sealed cannisters for later analysis.

In another embodiment, the sample is passed through an adsorbent trap, which adsorbs and retains the analyte of interest. The trap is subsequently analyzed for presence of the adsorbed analyte, for example, by desorption of the analyte from the trap. A variety of adsorbent materials may be used for this purpose, including, by way of example and not limitation, adsorbent resins such as Tenax TA, Tenax GR, and activated charcoals, particularly for trapping volatile and semi-volatile organics from gas or liquid samples.

Other types of adsorbents included $C_{18}$ reversed phase media, silica gel, ion-exchange resins, and others as is known in the art. Various forms of traps include filters cassettes (e.g., glass or polymeric filters with adsorbent material); annular denuders, which are constructed of metal or plastic concentric tubes coated with an absorbent or reactive chemical layer which traps analytes from a rapidly flowing stream; and simple tubes or containers containing the adsorbent materials. Other types of traps include impingers, which traps analytes of interest in a liquid solution, such as by use of an analyte derivatization reagent, and cryogenic traps, which passes the gas over a cold trap (i.e., liquid nitrogen, solid $CO_2$, refrigerant based system, etc) to condense the gas in the trap.

Thus, in one aspect, the carrier fluid transported to the surface is first collected in a collection means and then evaluated using various methods, such as chromatographs, chemical assays, bioassays, immunoassays or toxicity assays. Suitable collection means for this purpose include, but are not limited to, tubes, containers, flasks, cans, bottles, plates or vials.

In another embodiment, one of the transfer channels is connected to an analytical instrument. In this embodiment, the carrier fluid is transferred to a site where the samples can be collected and tested by the analytical instrument. Suitable analytical instruments include, by way of example and not limitation, gas chromatographs (GC), liquid chromatographs (e.g., high pressure liquid chromatography—HPLC), fluorescence detectors, polarograph analyzers, conductivity meters, ion selective electrodes, atomic absorption spectrometer, inductively coupled plasma emission spectrometer (ICP), metal oxide semiconductor (MOS) sensors, mass spectrometers (MS), gas ionization sensors, capillary electrophoresis, or combinations thereof, such as GC-MS, HPLC-MS and other appropriate detector combinations. The analytical instrument may be connected directly to the sampling device through one of the channels. Specific analytical instruments that may be directly connected to the transfer channel include, as examples, photoionization detector, flame ionization detector, thermal conductivity detector, halogen specific detector, nitrogen/phosphorous detector, and/or fluorescence detector. When an absorbent trap or sampling reservoir (e.g., loop) is used to collect the sample, useful analytical instruments include, as examples, gas chromatographs, GC-MS, HPLC, PHPLC-MS, capillary electrophoresis, and ICP-MS. The analytical instrument may be connected to a data acquisition system, such as through use of a computer, which stores the results of the analysis and/or transmits the data (e.g., through wire or wireless transmission) to a central information processing device or location.

The sampling system of this invention allows the detection and assessment of analytes of interest, such as SVOs or VOCs, without removing the sampling chamber from the difficult-to-reach or relatively inaccessible location. In one embodiment, the method for obtaining a sample for analysis comprises positioning or placing a sampling probe or sampling system, which contains the sampling device, in a sampling location. As used herein, "implant probe" or "sampling probe" or "sampling system" comprises the sampling device configured for placement into the sampling position, and thus may include an implanting tip, the protective housing or layer, and the shell or casing. The analyte of interest is then allowed to permeate through the semipermeable membrane into the chamber of the sampling device. Generally, the chamber contains a carrier fluid into which the analyte dissolves. The sampling device may be placed in any sampling location, particularly hard-to-reach or relatively inaccessible location, for sampling or monitoring of the analyte or analytes of interest. In one embodiment, the sampling chamber is implanted underground, in subsurface strata or groundwater, to collect analytes of interest in the underground surroundings. The underground sampling location may contain fluids, such as water or petroleum, or gases. In another embodiment, the sampling device is placed underwater, for instance, in a well, lake, or river. The method for installing the sampling device comprises directing the sampling probe into a sampling location by any method well known in the art. An exemplary method is drilling a path into the substrata and inserting the sampling device into the preformed path.

In another embodiment, the sampling device is disposed, attached, mounted, or housed in a tip assembly used to place the sampling device into the ground. The tip assembly comprises a sampling device disposed, attached, mounted, or fastened to a probe tip or probe, which permits insertion of the sampling device into the ground, substrata, or to any other sampling location. The probe tip engages, mates, or contacts the shell or casing protecting the sampling device. Contact of the tip with the shell may occur directly, or through an intermediary layer, such as a layer of resilient material (e.g., metal, plastic, graphite composite, etc.). A grooved section on the outer edge of the probe tip may be used to engage or mate the tip to the shell. In another embodiment, a guide member on the probe tip is used to engage the shell. The guide member may be formed discretely from the probe tip and is affixed thereto, or formed by attaching the guide member to the surface of the probe tip. Mating or engaging of the shell and the probe tip maintains the probe tip and the shell together, and thus limits appreciable movement of the probe tip away from the direction of insertion while positioning the sampling device in the sampling location. The tip assembly may be expendable, and is left in the sampling location upon withdrawal of the protective shell from the tip. The tip or probe is in any form or shape suitable for placing the sampling device in the sampling location. Exemplary forms or shapes of the probe tip in the region distal to the sampling device include, by way of example and not limitation, rounded, parabolic, conical, pyramidal, helical, screw, spiral, domed, etc. For the purposes of placing the tip into the ground or substata, the distal region of the probe tip may further comprise a hardened material, or a layer of hardened material, such as titanium or diamond layer, useful for facilitating inserting, boring, or drilling into subsurface material. For underwater applications, the sampling device may be weighted and permitted to sink to the desired depth.

Following placement of the sampling device in the sampling location, the protective shell encasing the transfer channels and/or chamber is removed or retracted to expose the sampling device to the surrounding environment for monitoring. In certain situations, such as underground placements, the space left after removal of the shell may be filled with an inert material to maintain the sampling device in a stable position while allowing contact of the sampling chamber with the environment. The inert materials include, by way of example and not limitation, sand or gravel, or mixtures thereof.

In addition, when the sampling device is placed underground, the space between the sampling device and the ground surface may be sealed with an appropriate sealant to prevent contamination or alteration to the monitored surroundings. For example, after placing the sampling device in a well, the opening to the well, and any other access points, may be sealed to prevent flow of contaminated materials into the well. Suitable sealing materials include, by way of example and not limitation, bentonite, grout, cement, silicone sealant, or other sealants as is known in the art.

A single sampling device may be used in one sampling location to detect the presence of the analyte of interest. In another aspect, an array of sampling devices may be positioned at different sampling locations to provide monitoring over a broad area. If different analytes are being examined, sampling devices with different types of semipermeable membranes may used at the different locations. Each sampling device in an array is positioned at different vertical and/or horizontal locations (e.g., multilevel installation at different depths). For instance, sampling devices positioned at different underground depths provide a way of determining the presence of analyte at different regions of an aquafer or underground water source. This type of array is useful where spread of contaminants is being monitored to determine the spatial pattern of underground contamination. It is to be understood that while the embodiments shown in the figures are driven vertically into the difficult-to-reach location where sampling is to occur, the probe can also be inserted at any angle desired to reach the desired region.

Once the sampling device is positioned in the sampling location, the materials to be analyzed are allowed to contact the sampling device, and the analytes allowed to permeate into the chamber. Various factors can affect the accumulation of the analytes of interest through the semipermeable membrane. Exemplary factors include the size of the semipermeable membrane, the membrane sampling rate, temperatures, flow rates or turbulence, the exposure duration, and the level of fouling or coating of the exterior membrane surface. Accordingly, calibration may be carried out to determine the performance of the semipermeable membrane and the sampling device. For instance, the sampling device is immersed in standard solutions containing differing amounts of the analyte of interest in different solvents, or in different types of gases containing a gaseous analyte. Different pressures and temperatures may be applied to examine effect of these factors on membrane characteristics. Permeation of the analyte into the chamber is then determined at various time intervals to calibrate the sampling device. In addition, the results obtained using the sampling device can be compared to the conventional sampling methodologies to verify the accuracy of the device.

To monitor or measure the level of analyte of interest in a sampling location, various methodologies may be employed. In one embodiment, the carrier fluid is transported to the surface for analysis after the analyte of interest reaches an equilibrium with the carrier fluid in the sampling chamber. In another embodiment, the carrier fluid is transported to the surface for analysis after the analyte of interest is allowed to permeate through the semipermeable membrane for a selected period of time. In each of these two embodiments, the sample may be delivered to the surface by pushing into the transfer channels a sufficient volume of fluid to cause the carrier fluid in the sample chamber to be delivered to the surface. To limit dilution of the analyte in a carrier fluid, the volume of the carried fluid is not substantially disturbed during the transfer from the sampling chamber to the surface. Transporting of the carrier fluid through the first channel to the sample delivery site may be carried out at timed intervals to monitor presence of analyte over a specified time period.

Using the sampling device and the sampling system described herein, various types of analytes may be sampled with the sampling device. In one aspect, the analytes comprise semivolatile or volatile organic compounds. Exemplary volatile organic compounds include, by way of example and not limitation, benzene, carbon tetrachloride, chlorobenzene, o-dichlorobenzene, p-dichlorobenzene, 1,1-dichloroethylene, cis-1,2-dichloroethylene, trans-1,2-dichloroethylene, dichloromethane, 1,2-dichloroethane, 1,2-dichloropropane, ethylbenzene, styrene, 1,2,4-trichlorobenzene, 1,1,1,-trichloroethane, 1,1,2-trichloroethane, trichloroethylene, tetrachloroethylene, toluene, vinyl chloride, xylenes, methyl-t-butyl ether (MTBE), ethanol, and the like.

Exemplary semivolatile compounds include, by way of example and not limitation, polyaromatic hydrocarbons, polychlorinated biphenyls, pesticides, herbicides, etc. Exemplary pesticides include, among others, 2,4-D, atrazine, carbaryl (Sevin), chlordane, chlorpyrifos (Dursban), cypermethrin, dichloro-diphenyl-trichloroethane (DDT), dieldrin, dioxin, deltamethrin, diazinon, fipronil, imidacloprid, lindane, malathion, methyl bromide, permethrin, pyrethrins, etc. Exemplary herbicides include, among others, atrazine, simazine, fluazifop-p-butyl, feneron, diuron, paraquat, glyphosate (Roundup), etc.

Included within the class of detectable analytes are degradation products of the compounds indicated above, such as degradation products of pesticides and herbicides These degradates, also referred to as metabolites or transformation products, are formed as compounds break down to different compounds in the environment. As the parent compounds may be detected by the device and the methods provided herein, the degradation products may be sampled and detected similarly. Degradation products of various compounds described herein will be well known to those skilled in the art.

In another aspect, the analytes sampled are metals and metal ions, or inorganic ions. Metals are generally present as metal ions complexed with counterions, and thus are usually found in the form of metal salts. Exemplary metals, many of which are present in the environment as metal ions, include, by way of example and not limitation, lead, chromium, mercury, copper, calcium, cadmium, magnesium, iron, zinc, etc. Exemplary inorganic ions, include, by way of example and not limitation, arsenic, perchlorate, nitrate, bromate, chlorate, phosphate, etc. Many of the inorganic ions are byproducts of fertilizers or fertilizer degradation, byproducts of water treatment processes, or effluents from industrial discharges, while others originate from natural sources, such as rock or mineral deposits. Many of these analytes leach through the ground, particularly when the analyte is soluble in water and is not readily adsorbed by the soil, and are common contaminants of water sources, such as wells and aquafers.

In addition to analytes present in liquids, the sample device may be used to detect gaseous analytes. The gas may permeate into the chamber when the gas is dissolved in a liquid, or the gas may permeate into the chamber directly from a gas source. Any type of gas diffusible across a semipermeable membrane may be sampled. The gases may be toxic, combustible, explosive, or corrosive. Exemplary gases that may be sampled and detected by the sampling device include, by way of example and not limitation, oxygen, carbon dioxide, carbon monoxide, radon, nitrogen dioxide, hydrogen sulfide, sulfur dioxide, methane, propane, chlorine, and hydrogen.

In another embodiment, the analytes are biological materials, including, by way of example and not limitation, proteins, viruses, rickettsia, bacteria, protozoa, and the like.

Porous semipermeable membranes are useful for these analytes since they are particulate in nature. A porous membrane permeable to the biological material of interest, but which excludes undesired analytes, may be used in the sampling device. Analytical techniques useful for detecting biological analytes, include, by way of example and not limitation, polymerase chain reaction assays; immunoassays, such as ELISA and immunhistochemistry; or gorwth assays (e.g., culturing the organisms under suitable culture conditions).

An exemplary sampling device, sampling systems, and methods of use described above are provided in the figures. FIG. 1 illustrates an exemplary sampling system of the present invention and its implantation below a soil surface. The implantation can be achieved using a membrane implant probe 2 comprising the sampling device. The expendable tip 8 of the implant probe 2 can be pushed through soil 4 into a stratum of interest, such as a region of groundwater 6. Direct push technology, such as Geoprobes or cone penetrometers, can be used. The implant probe 2 includes a retractable shell 7 which (at best seen in FIG. 2) contains a housing 16 that protects the transfer channels enclosed therein. The housing 16 and/or the transfer channels preferably are rigid to prevent collapse from pressure of the surrounding soil and/or water after the withdrawal of the probe shell 7. They may also be impermeable or have limited permeability to the analyte of interest over the timeframe of monitoring.

Once the probe has been pushed to the desired depth, the push rod or shell 7 can be retracted, leaving the expendable tip 8 in place and exposing the sampling device 10 with the transfer channels running to the surface (see FIG. 3). Sand 12 or a similar largely inert, granular or porous substance may be placed around the sampling device 10, which is protected from damage by a stainless steel cage 30 (see FIG. 3). The sand and protective cage hold the sampling device 10 in place while allowing flow of groundwater around the device. The rest of the installation hole will be either grouted or filled with bentonite 14 or other appropriate sealants, depending on site requirements, to effectively seal the hole to prevent surface contamination from running down into the groundwater 6 and thereby producing erroneous measurements.

FIG. 3 depicts a detailed view of the sampling device 10. The semipermeable membrane 28 is in the form of a hollow fiber loop capable of holding the carrier fluid. The semipermeable membrane 28 is held in place by a membrane support 26. The membrane is protected against crushing by a surrounding stainless steel cage 30. The two ends (28a and 28b) of the hollow fiber loop are connected to two transfer channels 21 and 22, respectively. As shown in FIG. 5, one of the transfer channels, 22, can be attached to an analytical device 24 at a sample delivery site. The other transfer channel 21 can be attached to a pumping system 20 or a source of pressurized fluid 18. Suitable fluids for this purpose include, but are not limited to, air, nitrogen, helium, other inert gas, water, or other environmentally benign liquid fluids. Delivery of the pressurized fluid into channel 21 causes the carrier fluid in the sample chamber to be driven via channel 22 to the analytical device 24.

FIG. 4 provides a detailed view of an exemplary tip assembly used to place the sampling device in an underground sampling location. The tip assembly comprises the sampling device 10 attached to a tip 8, which is a hardened metal for inserting into the substrata. The cage 30 protects the hollow fiber tube 28 of the sampling device. A protective layer or housing 16 surrounds the transfer channels, 21 and 22. The shell or casing 7 encloses the sampling device and transfer channels and protects them from damage during placement of the sampling device. The shell is made removable or retractable for exposing the sampling device to the sampling environment.

Periodically, the groundwater in an area or a level of soil stratum 6 can be assessed using the sampling system of this invention (see FIG. 5). Once the sampling device 10 is in place and surrounded by sand or some other porous medium 12, a pump 20 or the source of pressurized fluid 18 can be attached to one of the transfer channels (21). The other transfer channel (22) can be attached to an analytical device 24. After volatiles or semivolatiles present in the groundwater or subsurface stratum 6 permeate into sampling device containing the carrier fluid 10, fluid can be driven from one transfer channel (21) to the other (22), pushing the carrier fluid in the sampling device chamber to the surface for analysis by the analytical device 24. In this fashion, sampling can be performed more easily, less expensively, and more reliably than with conventional approaches.

In one embodiment, the carrier fluid in the sampling chamber can include multiple types of fluids which form a sandwich or sequence of carrier fluid volumes. These different fluids preferably are immiscible with each other. They can be placed in the sampling chamber, such as the hollow fiber loop in FIG. 3, simultaneously or in succession. This provides an opportunity for distinct sampling events. Alternatively, distinct immiscible volumes of carrier fluids may be used as marker layers for other sample volumes.

In another embodiment, as discussed above two or more sampling chambers can be used in the sampling system of this invention. Different sampling chambers may contain different semipermeable membranes, thereby allowing discriminable detection of various analytes of interest at the same time.

It should be understood that the above-described embodiments and the following example are given by way of illustration and are not intended to be exhaustive or to limit the invention to the precise forms disclosed. Various changes and modifications within the scope of the descriptions provided herein will become apparent to those skilled in the art in light of the teachings given herein.

All patents, patent applications, publications, and references cited herein are expressly incorporated by reference to the same extent as if each individual publication or patent application was specifically and individually indicated to be incorporated by reference.

EXAMPLES

Example 1

FIGS. 6–8 display data collected from a laboratory-based hollow-fiber membrane sampler (HFM). The sampler was constructed by affixing a half-meter length of silicone tubing (0.077 in. O.D.; 0.058 in. I.D.) to 6 inch sections of PEEK tubing (0.062 in. O.D.; 0.030 in. I.D.). This membrane was immersed in a saturated solution of naphthalene and benzo (a)pyrene then filled with distilled water. The system was allowed to equilibrate for 24 hours before air was used to flush the solution into a collection vial. The resulting solution was analyzed with a SPEX FluoroMax-2 spectrofluorimeter.

Example 2

FIG. 6 shows laboratory data collected from a HFM in a naphthalene and benzo(a)pyrene saturated water solution. FIG. 7 shows normalized data from inside and outside the HFM.

The polyaromatic hydrocarbon (PAH) fluorescence spectrum from inside the HFM shows excellent correlation with the spectrum from outside the HFM. The intensity of the fluorescence signal from inside is approximately 80% of the signal from outside the HFM. However, the PEEK transfer lines were also filled with water so some dilution of the sample is likely. This data demonstrates that PAHs readily pass through the membrane of the HFM.

Example 3

FIG. 8 shows data collected with another HFM and a coal tar sample. This HFM was constructed using the same procedure as described above. The sample solution was prepared by placing water in intimate contact with a coal tar sample and allowing the sample to equilibrate for several days. The coal tar saturated water was then extracted and filtered prior to use. The membrane was immersed in this saturated solution and then filled with distilled water. The system was allowed to equilibrate for four hours before air was used to flush the solution into a collection vial. The resulting solution was again analyzed with a SPEX Fluoro-Max-2 spectrofluorimeter.

What is claimed:

1. A sampling device for detecting an analyte of interest in a difficult-to-access sampling location, comprising:
    a chamber having at least one part of a wall of the chamber defined by a semipermeable membrane;
    the semipermeable membrane, wherein the semipermeable membrane is permeable to the analyte of interest;
    a first channel communicating with the chamber;
    a second channel communicating with the first channel through the chamber,
    wherein the first channel and the second channel enable a carrier fluid to be transported from the chamber to a sample delivery site; and
    a source of pressurized fluid communicating with at least one of the first and second channels for selectively causing a volume of the carrier fluid to remain in the chamber in contact with the semipermeable membrane for a specified equilibration period and thereafter transporting at least a portion of the volume to a sample delivery site.

2. The sampling device of claim 1 further comprising a protective layer surrounding the first channel and the second channel.

3. The sampling device of claim 1 further comprising a shell surrounding the chamber.

4. The sampling device of claim 3, wherein the shell surrounds the first channel and the second channel.

5. A sampling device, for detecting an analyte of interest in a difficult-to-access sampling location, comprising:
    a chamber having at least one part of a wall of the chamber defined by a semipermeable membrane;
    the semipermeable membrane, wherein the semipermeable membrane is permeable to the analyte of interest;
    a first channel communicating with the chamber; and
    a second channel communicating with the first channel through the chamber,
    wherein a removable shell surrounds at least one of (i) the chamber or (ii) the first channel and the second channel, and the first channel and the second channel enable a carrier fluid to be transported from the chamber to a sample delivery site.

6. The sampling device of claim 3 or 4, further comprising a probe tip for insertion of the sampling device into the sampling location, wherein the probe tip engages the shell and the sampling device is disposed on a surface of the probe tip.

7. The sampling device of claim 1, further comprising a sample collector and with the source of pressurized fluid connected to the second channel, wherein the pressurized fluid is capable of driving the carrier fluid from the chamber through the first channel to the sample collector.

8. The sampling device of claim 1, further comprising:
    an analytical instrument communicating with the chamber through the first channel;
    and with the source of pressurized fluid connected to the second channel, wherein the pressurized fluid is capable of driving the carrier fluid from the chamber through said first channel to the analytical instrument.

9. The sampling device of claim 7 or 8, wherein a pump is the source of the pressurized fluid.

10. The sampling device of claim 1, wherein the semipermeable membrane is in the shape of a tube and the internal space of the tube comprises the chamber.

11. The sampling device of claim 10, wherein the tube comprises a silicone tube.

12. An array of sampling units, wherein each of the sampling units comprises the sampling device of any one of claim 1 to 5 positioned at a different sampling location.

13. The array of sampling units of claim 12, wherein the different sampling location is at a different horizontal location.

14. The array of sampling units of claim 12, wherein the different sampling location is at a different vertical location.

15. A method of obtaining a sample for detecting an analyte of interest in a difficult-to-access location, comprising the steps of:
    a) positioning the sampling device of claim 1 in a sampling location;
    b) allowing the analyte of interest to permeate through the semipermeable membrane into the chamber, wherein the chamber contains a carrier fluid; and
    c) transporting the carrier fluid from the chamber through the first channel.

16. The method of claim 15, wherein the transporting of the carrier fluid is to a sample collector.

17. The method of claim 15, wherein the transporting of the carrier fluid is to an analytical instrument.

18. The method of claim 15, wherein transporting the carrier fluid from the chamber through the first channel occurs at periodic intervals.

19. A method of installing a sampling system, comprising:
    a) directing a sampling probe to a sampling location, wherein the probe comprises a sampling device enclosed in a shell, said sampling device being for detecting an analyte of interest in a difficult-to-access sampling location and comprising:
    a chamber having at least one part of a wall of the chamber defined by a semipermeable membrane;
    the semipermeable membrane, wherein the semipermeable membrane is permeable to the analyte of interest;
    a first channel communicating with the chamber; and
    a second channel communicating with the first channel through the chamber, wherein the first channel and the second channel enable a carrier fluid to be transported from the chamber to a sample delivery site; and
b) withdrawing the shell.

20. The method of claim 19, further comprising filling the spaces previously occupied by the shell.

* * * * *

UNITED STATES PATENT AND TRADEMARK OFFICE
CERTIFICATE OF CORRECTION

| | | |
|---|---|---|
| PATENT NO. | : 6,978,688 B2 | Page 1 of 1 |
| APPLICATION NO. | : 10/698715 | |
| DATED | : December 27, 2005 | |
| INVENTOR(S) | : Daniel S. Engebretson | |

It is certified that error appears in the above-identified patent and that said Letters Patent is hereby corrected as shown below:

Column 1, line 9, after "reference," and before the heading "TECHNICAL FIELD" insert a new heading and a new paragraph to read as follows:

--STATEMENT REGARDING FEDERALLY SPONSORED RESEARCH OR DEVELOPMENT

The work described herein was supported in part by Grant Number 5 R43 ES011876-02 awarded by the National Institute of Health. The U.S. Government has certain rights to this invention.--

| | Reads | Should Read |
|---|---|---|
| Col. 15, line 8 | "gorwth" | --growth-- |

Signed and Sealed this

Seventh Day of November, 2006

JON W. DUDAS
*Director of the United States Patent and Trademark Office*